(12) United States Patent
Li

(10) Patent No.: US 11,116,876 B2
(45) Date of Patent: Sep. 14, 2021

(54) METHODS AND DEVICES FOR REPAIR OF SEVERED PERIPHERAL NERVES WITH ERYTHROPOIETIN

(71) Applicant: STL Laboratories Inc., Franklin Lakes, NJ (US)

(72) Inventor: Shu-Tung Li, Wyckoff, NJ (US)

(73) Assignee: Shu-Tung and Alice Li Foundation Inc., Franklin Lakes, NJ (US)

( * ) Notice: Subject to any disclaimer, the term of this patent is extended or adjusted under 35 U.S.C. 154(b) by 0 days.

(21) Appl. No.: 16/280,424

(22) Filed: Feb. 20, 2019

(65) Prior Publication Data

US 2019/0255220 A1 Aug. 22, 2019

Related U.S. Application Data

(60) Provisional application No. 62/632,619, filed on Feb. 20, 2018.

(51) Int. Cl.
| | | |
|---|---|---|
| *A61L 27/44* | (2006.01) | |
| *A61L 27/54* | (2006.01) | |
| *A61L 27/56* | (2006.01) | |

(52) U.S. Cl.
CPC ............ *A61L 27/44* (2013.01); *A61L 27/54* (2013.01); *A61L 27/56* (2013.01); *A61L 2300/252* (2013.01); *A61L 2300/43* (2013.01); *A61L 2430/32* (2013.01)

(58) Field of Classification Search
None
See application file for complete search history.

(56) References Cited

U.S. PATENT DOCUMENTS

| | | | |
|---|---|---|---|
| 5,024,841 A | | 6/1991 | Chu et al. |
| 5,026,381 A | * | 6/1991 | Li ..................... A61B 17/1128 606/152 |
| 5,756,457 A | | 5/1998 | Wang et al. |
| 6,489,293 B1 | | 12/2002 | Sytkowski et al. |
| 6,716,225 B2 | | 4/2004 | Li et al. |
| 6,955,524 B2 | | 10/2005 | Stengel |
| 8,821,917 B2 | | 9/2014 | Li et al. |
| 2004/0018978 A1 | | 1/2004 | Campana et al. |
| 2010/0158800 A1 | * | 6/2010 | Mckay ................. A61K 9/0024 424/1.29 |
| 2013/0345729 A1 | | 12/2013 | Li et al. |
| 2015/0044259 A1 | | 2/2015 | Desilva |
| 2016/0038419 A1 | * | 2/2016 | Elfar .................. A61K 31/4409 424/489 |

FOREIGN PATENT DOCUMENTS

| | | |
|---|---|---|
| EP | 2674166 A1 | 12/2013 |
| WO | WO-2013/072409 A1 | 5/2013 |

OTHER PUBLICATIONS

Aydin et al (Journal of Clinical and Analytical Medicine, (Year: 2018).*
European Medicines Agency (Nov. 20, 2014) (Year: 2014).*
Archibald et al "Monkey Median Nerve Repaired by Nerve Graft or Collagen Nerve Guide Tube" The Journal of Neurosciences vol. 15, pp. 4109-4123, 1995.
Chamberlain et al "Near-Terminus Axonal Structure and Function Following Rat Sciatic Nerve Regeneration Through a Collagen-GAG Matrix in a Ten-Millimeter Gap" Journal of Neurosciences Research vol. 60, pp. 666-677, 2000.
De Medinaceli et al "An Index of the Functional Condition of Rat Sciatic Nerve Based on Measurements Made from Walking Tracks" Experimental Neurology vol. 77, pp. 634-643, 1982.
Fowler et al "Analysis of Myelin and Neurofilament Content in a Sciatic Nerve Crush Injury Model" Journal of Nature and Science vol. 1, pp. 1-5, 2015.
Geary et al "Erythropoietin Accelerates Functional Recovery Following a Moderate Sciatic Nerve Crush Injury" Muscle Nerve vol. 56, pp. 143-151, 2017.
Lundborg "A 25-Year Perspective of Peripheral Nerve Surgery: Evolving Neuroscientific Concepts and Clinical Significance" The Journal of Hand Surgery vol. 25A, pp. 391-414, 2000.
Moldovan et al "Comparison of the Fastest Regenerating Motor and Sensory Myelinated Axons in the Same Peripheral Nerve" Brain vol. 129, pp. 2471-2483, 2006.
Sundem et al "Erythropoietin Enhanced Recovery After Traumatic Nerve Injury: Myelination and Localized Effects" The Journal of Hand Surgery, 2016.
Yin et al "Erythropoietin Promotes Functional Recovery and Enhances Nerve Regeneration After Peripheral Nerve Injury in Rats" American Journal of Neuroradiology vol. 31, pp. 509-515, 2010.

\* cited by examiner

*Primary Examiner* — Celeste A Roney
(74) *Attorney, Agent, or Firm* — Cesari & McKenna, LLP

(57) ABSTRACT

An implantable drug-delivery device for repairing a severed peripheral nerve. The drug-delivery device includes a matrix formed of a biopolymer and an erythropoietin (EPO) entrapped in the matrix. After in vivo implantation of the drug-delivery device, the EPO elutes over a period of 1 day to 12 weeks. Also disclosed is a method for repairing a severed peripheral nerve using the implantable drug-delivery device.

25 Claims, No Drawings

METHODS AND DEVICES FOR REPAIR OF SEVERED PERIPHERAL NERVES WITH ERYTHROPOIETIN

CROSS-REFERENCE TO RELATED APPLICATIONS

This application claims priority of U.S. Provisional Application No. 62/632,619, filed on Feb. 20, 2018.

BACKGROUND

The major clinical objective in the repair of severed peripheral nerves is to restore continuity between the proximal and distal nerve stumps, without which functional recovery is virtually impossible.

Severing axonal fibers in a peripheral nerve induces a significant degree of intracellular perturbation and reorganization in the cell bodies located in the spinal cord, in preparation for repair of the damaged nerve fibers. The period of injury information transmittance, intracellular reorganization, and preparation for subsequent repair is referred to as the post-surgery latency period. The latency period is generally 1 to 3 weeks. See, e.g., Moldovan, et al., 2006, Brain 129:2471-2483; and Archibald et al. 1995, J. Neurosci. 15:4109-23.

After the latency period, axons from the proximal stump will sprout, extend in length, and attempt to reach its end target organ. The length of the latency period depends in part on the length of the nerve gap injury. The distal nerve stump contains neurotrophic factors which influence the behavior of the proximal stump and the latency time. As such, in a short gap, the distal stump will be close enough to the proximal stump to influence the repair. Indeed, direct suture repair for short gaps (<1 cm) generally result in satisfactory return of function.

When the gap increases beyond a certain length, about 2 cm in humans, the influence of distally released neurotrophic factors decreases. The distal part of the nerve will undergo Wallerian degeneration, resulting in an inflammatory response for removing degenerated cell debris and in laying down of new scar-like connective tissue. As a result, axons will stop growing and form a tapered end at the nerve terminal. See, e.g., Lundborg, J. Hand Surg. 2000, 25A:391-414.

For large nerve gaps, autograft of a peripheral nerve harvested from the patient, such as a sural nerve autograft, is the preferred treatment. Unfortunately, nerve autografting often results in axonal escape at the suture lines, which reduces the number of axons reaching the end organ. In addition, axonal escape at the suture line can lead to painful neuroma formation. Other complications include graft survival, size mismatch and second surgery associated complications.

As an alternative, several type I collagen tubular nerve guide products have been approved for so-called entubulation repair of peripheral nerve gaps of 2 cm or smaller.

Recent studies have shown that erythropoietin (EPO) has protective effects on Schwann cells and neurons, leading to restoration of myelin and speedy recovery of nerve injuries. See, e.g., Fowler et al. 2015, J. Nature and Science, 1(8): e166; Sundem et al. 2016, J. Hand Surg. Am. 41:999-1010; Yin, et al., 2018, Am. J. Neuroradiol. 31:509-15; and Geary et al. 2017, Muscle Nerve 56:143-151.

Methods and devices are needed to (i) shorten the latency period and thus the onset of axonal sprouting and growth, (ii) accelerate the myelination of regenerated axons, (iii) increase the total number of myelinated axons across the gap in a severed nerve, (iv) improve the speed of myelination and the extent of functional recovery, and (v) increase the length of the gap that can be successfully repaired.

SUMMARY

To meet the needs set forth above, an implantable drug-delivery device for repairing a severed peripheral nerve is provided. The drug-delivery device includes a matrix formed of a biopolymer and an erythropoietin (EPO) entrapped in the matrix. After in vivo implantation of the drug-delivery device, the EPO elutes over a period of 1 day to 12 weeks.

Also disclosed is a method for repairing a severed peripheral nerve. The method includes (i) providing an implantable drug-delivery device that includes a matrix formed of a biopolymer and an EPO entrapped in the matrix, (ii) attaching the distal peripheral nerve stump to the proximal peripheral nerve stump via a nerve guide implant, and (iii) implanting the drug-delivery device at the site of the severed peripheral nerve. After implantation in vivo of the drug-delivery device, the EPO elutes from the device over a period of 1 day to 12 weeks.

The details of one or more embodiments of the invention are set forth in the description below. Other features, objects, and advantages of the invention will be apparent from the description and from the claims.

DETAILED DESCRIPTION

As mentioned above, an implantable drug-delivery device for repairing a severed peripheral nerve is provided that includes a matrix formed of a biopolymer.

The matrix can be a porous de-cellularized biopolymer-based extracellular matrix (ECM) of a mammalian peripheral nerve. The ECM is free of cells and is free of any immunogenic material. In another aspect, the matrix can be a porous matrix formed of collagen.

Alternatively, the matrix is semi-permeable and is formed of a biopolymer that can be, but is not limited to chitosan, alginic acid, cellulose, elastin, fibrin, a glycosaminoglycan, gelatin, or a collagen. The matrix can be formed of a mixture of these biopolymers.

The collagen is a fiber-forming collagen, e.g., collagen type I, type II, or type III, having a native structure. In other words, the device is free of denatured or cleaved collagens. In a particular device, the collagen is type I collagen.

The implantable drug-delivery device also includes an erythropoietin (EPO) entrapped in the matrix. The EPO can be purified natural EPO, recombinant EPO produced in bacteria or mammalian cells, or an EPO mimetic. See, e.g., U.S. Pat. No. 6,489,293.

As mentioned above, after in vivo implantation, the EPO elutes from the device over a period of 1 day to 12 weeks. For example, the EPO can elute over a 1 day to 7 day period, a 1 to 3 week period, a 3 to 6 week period, and a 6 to 12 week period. Any intermediate elution time between 1 and 12 weeks falls within the scope of the present invention.

Alternatively, the EPO can elute on a short-term basis, i.e., on the order of hours and even on the order of days. For example, a device is disclosed in which, following in vivo implantation, the EPO elutes over 1, 2, 4, 8, 12, 16, and 24 hours or over 2, 3, 4, 5, 6, and 7 days.

The EPO elution time can be selected for a particular application. For example, for repairing a long, i.e., >3 cm, nerve gap, a device that, after in vivo implantation, elutes EPO over a 6 to 12-week period can be used. This long-term release of EPO is important for (i) maintaining the viability of existing cells in the severed nerve, (ii) protecting newly generated axons during the period of nerve regeneration, and (iii) re-establishing end organ, e.g., muscle, function.

In another example, a device for repairing a short, i.e., <1 cm, nerve gap can, after in vivo implantation, elute EPO on a short-term basis as described above. The short-term elution of EPO, i.e., from 1 to 7 days, can accelerate axon sprouting from the proximal nerve stump.

In yet another example, for repair of an intermediate-sized gap of 1-3 cm, two distinct devices are used. A first device that, after in vivo implantation, elutes EPO on a short-term basis is used in conjunction with a second device that, after in vivo implantation, elutes EPO over a 3-6 week period. As mentioned above, the short-term elution of EPO accelerates axonal sprouting. The elution of EPO over 3 to 6 weeks protects the existing nerve cells from degeneration in both the proximal and the distal ends of the nerve gap.

The device can be constructed in a number of shapes, depending upon the application. The shapes include, but are not limited to, a flat membrane, a strip, a block, a rod, a thin filament, a tube, and a tubular wrapping cuff, i.e., a tube cut open along its long axis.

In a particular example, the device is a tubular nerve guide device that contains EPO entrapped within its walls. Such a device serves as both a nerve guide and a drug-delivery device.

In another embodiment, the device is an intraluminal device. In this embodiment, the device contains a porous collagen matrix or a porous ECM of a mammalian peripheral nerve, and an EPO entrapped in the matrix. The device can be inserted into the lumen of a nerve guide for EPO release prior to entubulation repair of the severed nerve.

As mentioned above, a method for repairing a severed nerve is provided that includes a step of providing an implantable drug-delivery device that includes a matrix formed of a biopolymer and an EPO entrapped in the matrix. The device can be the same device described above. To reiterate, the matrix can be (i) a porous collagen matrix or a porous ECM of a mammalian peripheral nerve or (ii) a semi-permeable matrix formed of a biopolymer, e.g., chitosan, alginic acid, cellulose, elastin, fibrin, a glycosaminoglycan, gelatin, a collagen, and a mixture thereof. The collagen is a fiber-forming collagen, e.g., collagen type I, type II, or type III, having a native structure. The device is thus free of denatured or cleaved collagens. In a particular device, the collagen is type I collagen. The EPO entrapped in the matrix can be purified natural EPO, recombinant EPO produced in bacteria or mammalian cells, or an EPO mimetic, as set forth, supra.

The method for repairing a severed nerve also includes a step of attaching the distal stump to the proximal stump via a nerve guide implant. Nerve guide implants are known in the art. For example, the nerve guide implant can be a tubular collagen nerve guide as described in U.S. Pat. No. 6,716,225 and US Patent Application Publication 2013/0345729.

One end of the tubular nerve guide implant is sutured to the proximal nerve stump and the other end is sutured to the distal nerve stump.

Following implantation of the nerve guide, the drug-delivery device is implanted at the site of the severed nerve. In a particular method, the drug-delivery device is affixed to the outer surface of the nerve guide implant. For example, the drug-delivery device in the form of a thin strip can be wrapped around one end of the tubular nerve guide implant. In a specific example, the drug-delivery device is wrapped around the end of the tubular nerve guide implant that was sutured to the proximal nerve stump. In yet another example, the drug-delivery device in the form of a flat membrane is wrapped around the entire length of the nerve guide implant. Alternatively, the drug-delivery device can be in the form of a tubular cuff having an inside diameter approximately the same as the outside diameter of the nerve guide implant. In this instance, the drug-delivery device is wrapped around the nerve guide implant and stays in place without the need for sutures.

Further, the drug-delivery device can be sutured to the nerve guide implant or it can be affixed to it using a glue, e.g., a fibrin glue.

In an alternative method, the drug-delivery device is affixed to the inner surface of the nerve guide implant prior to attaching the nerve guide implant to the ends of the severed nerve. The drug-delivery device can be affixed at one end of the nerve guide implant or along its entire length.

In yet another method, the drug-delivery device is an intraluminal device containing a porous collagen matrix or a porous ECM of a mammalian peripheral nerve, and an EPO entrapped in the matrix. In this method, the drug-delivery device is inserted into the lumen of a nerve guide prior to suturing the severed nerve stumps to the nerve guide.

Also within the scope of the invention is a method in which the drug-delivery device itself also serves as a nerve guide. In this method, the drug-delivery device in tubular form is sutured between the proximal and distal nerve stumps.

After implantation in vivo of the drug-delivery device, the EPO elutes from the device over a period of 1 day to 12 weeks. In an exemplary method, the gap between the proximal stump and the distal stump is 1 cm or less and the EPO elutes over 1 day to 7 days. In another example, the gap is 1 cm to 3 cm and the EPO elutes over 3 to 6 weeks. In a further example, the gap is 3 cm to 10 cm and the EPO elutes over 6 to 12 weeks.

In additional methods, two drug-delivery devices each having a distinct EPO elution period are implanted in vivo. In one example, the nerve gap is 3 cm to 10 cm and a first drug-delivery device that elutes EPO over 1 to 3 weeks is employed together with a second drug-delivery device that elutes EPO over 6 to 12 weeks.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entireties.

EXAMPLES

Example 1: Preparation of Collagen Membranes

A type I collagen membrane was prepared from purified type I collagen fibers as follows. Bovine Achilles tendon tissue from 6-12 month-old animals were cleaned, frozen, and sliced into 0.5 mm thick slices. Purified type I collagen fibers were obtained from the slices by performing a series of extractions with water, acid, base, alcohol, and a salt solution to remove non-collagenous material from the tissue essentially as described in U.S. Pat. Nos. 6,955,524 and 8,821,917.

An aliquot of the purified type I collagen fibers was suspended in 0.7 M lactic acid, pH 2.5 overnight at 4° C. and subsequently homogenized to reduce the fiber size and achieve a uniform dispersion. The pH of the solution was then adjusted to the isoelectric point (~pH 4.8) to reconstitute type I collagen fibers.

The reconstituted type I collagen fibers were partially dehydrated and laid on the surface of a flat polymer sheet, e.g., a polytetrafluoroethylene (PTFE) sheet. The collagen fibers were spread on the PTFE sheet by pressing them with a roller to form a matrix having a desired pore structure, thickness, and density.

More specifically, a fixed weight of partially dehydrated collagen fibers having a fixed amount of solid, i.e., collagen, per wet weight was compressed to a defined area and thickness, e.g., 0.1 mm to 2 mm, to achieve a defined wet matrix density. Upon freeze drying, a dry density in the range of 0.05 g/cm$^3$ to about 0.5 g/cm$^3$ was achieved. Within this density range the pore size is from about 100 µm to about 500 µm along the long axis of the pore. This pore size supports a permeability of macromolecules having a molecular weight of approximately 1,000,000 Dal or less.

The partially dehydrated membrane sheet formed as set out in the preceding paragraph was freeze-dried. The freeze-dried membrane sheet was subjected to chemical crosslinking using formaldehyde vapor to impart in vivo stability to the membrane.

Alternatively, the reconstituted type I collagen fibers mentioned, supra, were coated onto a rotating mandrel and partially dehydrated by pressing the fibers between a pair of glass plates. In this way, the thickness, density, and pore structure of the final implant were adjusted to suit its intended purpose.

The partially dehydrated tubular membrane was freeze-dried and then cut longitudinally prior to chemical crosslinking using formaldehyde vapor to impart in vivo stability to the membrane cross-linking.

Example 2: Preparation of Tubular Cuff Implant

A curled tubular cuff can provide uniform distribution of EPO around the proximal and distal stump regions, and can facilitate the placement of the drug-delivery device without disturbing the nerve guide sutures. An exemplary device was prepared as set forth below.

Purified collagen fibers were suspended in 0.07 M lactic acid (pH 2.3) at a final collagen content of 0.7% (w/v) and swollen by incubation at 4° C. overnight. The swollen fibers were then homogenized to reduce the fiber size to fibrils to obtain a uniform dispersion. After de-gassing under vacuum, the pH of the dispersion was adjusted to the isoelectric point of collagen (~pH 4.8) with 1 M $NH_4OH$ to reconstitute the dispersed collagen fibers.

The reconstituted collagen fibers were evenly wrapped around a rotating PTFE mandrel (OD 5.0 mm) to form a tubular membrane. Collagen fibers in the tubular membrane were partially dehydrated as described above in Example 1 using a thickness control gauge to form the tubular membrane with a fixed wall thickness (0.3 mm) to control its permeability.

The partially dehydrated tubular membrane was freeze-dried, removed from the mandrel, and subjected to chemical crosslinking. More specifically, crosslinking was performed with vapor from a 2% formaldehyde solution, followed by extensive washing with $H_2O$ to remove any residual formaldehyde.

After washing, the tubular membrane was freeze-dried and cut along its longitudinal axis to form a curled tubular cuff.

Example 3: Preparation of a Porous ECM Biopolymer Matrix

Porcine peripheral nerves were obtained from a local abattoir. The nerves were cleaned of extraneous tissues and washed with $H_2O$. A series of extraction steps were performed to remove potential immunogenic moieties from the ECM as follows: (i) cellular components and lipid moieties were removed with 2% polyethylene glycol tert-octylphenyl ether (TRITON™ X100); (ii) proteoglycans and glycosaminoglycans (GAG) were extracted with 3 M guanidine hydrochloride; (iii) removal of basic proteins and residual lipids via saponification was accomplished by extraction with 0.5 M NaOH/0.5 M $Na_2SO_4$; (iv) acidic proteins, acidic glycoproteins, and residual GAG were removed with 0.25 M HCl/0.5 M $Na_2SO_4$ extraction; (v) neutral salt soluble moieties were removed by extraction with 0.5 M NaCl; and (vi) remaining lipids were removed with isopropanol.

The nerve tissue thus extracted was rinsed with $H_2O$ repeatedly to remove any residual chemicals employed in the extraction process. The final ECM biopolymer matrix was freeze-dried and lightly crosslinked with formaldehyde vapor.

Example 4: Preparation of EPO/Collagen Matrix Implants for Short-Term and Intermediate-Term In Vivo EPO Release EPO was obtained from Bon Opus Biosciences (Summit, N.J.). The weight to bioactivity conversion was 1 ng of EPO to 1.2 IU. This relationship was determined as follows. A series of dilutions of EPO in saline was prepared over a concentration range of 1.5625 pg to 100 pg. The amount of EPO, expressed as IU, in each dilution was determined with an EPO ELISA kit as directed by the manufacturer (ThermoFisher Scientific, Waltham, Mass.). The concentration of EPO in each sample by weight was equated to the concentration in IU.

EPO (60,000 IU) was dissolved in 0.5 ml of phosphate buffered saline (PBS; pH 7.2) to make a stock solution. Samples of the stock solution were diluted with PBS to make solutions containing 12 IU, 120 IU, 900 IU, and 1,200 IU of EPO in 100 µl. Each EPO solution was uniformly added via a volumetric micro-pipettor to a curled tubular cuff delivery device.

In particular, a tubular collagen cuff was prepared as described in Example 2 above. The tubular cuff had an inside diameter of 5 mm and an outside diameter of 5.6 mm and a length of 20 mm. The pore sizes of the tubular collagen cuff were significantly larger than the size of EPO (M.W. 30.4 KDal, diameter ~20 Å) to prevent surface adsorption of the EPO.

EPO was allowed to diffuse into the interstitial, i.e., intrafibrillar, space through the pores of the tubular collagen cuff to form an EPO/collagen composite matrix. Not to be bound by theory, it is believed that the EPO interacted with the collagen fibers of the cuff via physical, mechanical, and electrostatic interactions.

The EPO/collagen composite matrix was then air dried.

Example 5: Preparation of EPO/Collagen Composite Matrices for Long-Term Sustained Release of EPO In Vivo Up to 12 Weeks To release EPO at a slow and sustainable rate, the EPO was entrapped within a collagen matrix during the reconstitution of collagen fibers as described above in Example 2. To accomplish this, a fixed amount of EPO (1,000 IU to 5000 IU) was dissolved in PBS, pH 7.2. The EPO solution was then mixed with a 0.7% (w/v) collagen dispersion, pH 2.3, prior to reconstituting the collagen fibers by adjusting the pH to the isoelectric point of collagen (pH 4.8) with 1 M NH$_4$OH. Under these conditions, EPO was co-reconstituted together with collagen fibrils.

Further processing and engineering the reconstituted yet still hydrated EPO/collagen fibers into an EPO/collagen cuff matrix was performed as described above in Example 2.

The EPO/collagen matrix was stabilized by formaldehyde vapor crosslinking to form a matrix that can be maintained for long periods of time in vivo. To avoid loss of EPO, residual formaldehyde was removed by venting for 72 to 96 h instead of by H$_2$O rinsing as in Example 2. The venting reduced the residual amount of formaldehyde to a level safe for in vivo implantation.

The desired in vivo stability of the EPO/collagen cuff matrix was controlled by the extent of formaldehyde crosslinking. The expected in vivo stability of the matrix was estimated by measuring hydrothermal shrinkage temperature of the matrix by differential scanning calorimetry.

The permeability of the collagen cuff matrix was adjusted during its formation in order to reduce the rate of diffusion of EPO so as to obtain sustained release over a longer period of time. For example, one way to reduce permeability is to increase the density of the engineered collagen cuff matrix. This was accomplished by more extensive dehydration of the reconstituted EPO/collagen cuff matrix prior to freeze-drying during the matrix engineering process.

Generally, the higher the density, the smaller the pore size, thus the slower the permeability, which in turn decreases the rate of EPO release.

At a density of 0.35-0.50 g/cm$^3$, only about 50% of the interstitial space in the EPO/collagen cuff matrix is open. As a result, the movement of EPO will be significantly restricted and the physical, mechanical, and electrostatic interactions are enhanced and stabilized to reduce the rate of release of EPO.

The length of the EPO/collagen cuff matrix was such that it would cover the length of a nerve gap defect and extend 2 mm beyond the gap to ensure that both the proximal and distal stump regions were covered.

Example 6: Determination of the Extent of EPO Incorporation

The incorporation efficiency of EPO for the short- and intermediate-term EPO/Collagen matrix implants described above in Example 4 was 100%, as all of the EPO solution delivered via micropipette was adsorbed into the matrix.

Turning to the sustained release EPO/collagen matrix implant of Example 5, EPO incorporation efficiency was determined by the weight difference between the total EPO added to the dispersion and the residual EPO left in the solution after the EPO/collagen matrix was reconstituted. EPO was measured by ELISA assay mentioned above in Example 4.

As a control, a length of collagen tubular cuff matrix was soaked in 1 ml of a solution of 550 IU/ml EPO, and the amount of EPO remaining in the solution measured by ELISA. The results are shown in Table 1 below.

TABLE 1

| Amount of EPO in Collagen cuffs | | | |
|---|---|---|---|
| | Soaking | Micropipette (Example 4) | Co-reconstituting (Example 5) |
| Initial EPO amount | 550 IU/ml | 12-1,200 IU/100 µl | 480 IU/5 ml |
| Absorbed EPO (IU) | 434 ± 11.6 | 12-1,200 | 463 |
| Efficiency of incorporation (%) | 78.8 ± 2.1 | 100 | 96.03 |

The efficiencies of EPO incorporation via micropipette and via co-reconstitution were similar, and both were higher than that achieved by soaking the collagen cuff matrix in an EPO solution.

Example 7: Kinetics of EPO Release In Vitro

To determine the rate and quantity of EPO release, 30 mg samples of each EPO/collagen composite matrices with known EPO quantity were incubated in 10 ml of PBS (pH 7.2) at 37° C. with constant shaking. Ten microliter aliquots of the PBS containing EPO released from the matrix samples were collected and EPO content determined by ELISA as described above. The results are shown in Table 2 below.

TABLE 2

| EPO release kinetics from collagen cuffs | | | | | | | | | | |
|---|---|---|---|---|---|---|---|---|---|---|
| EPO amount loaded | | days | | | | | | | | |
| | | 1 | 3 | 5 | 7 | 10 | 14 | 21 | 28 | 35 |
| 12 IU | amt. released | 0.04$^a$ | 0.07 | 0.07 | N.D.$^d$ | N.D. | N.D. | N.D. | N.D. | N.D. |
| | cumulative | 0.04$^b$ | 0.11 | 0.18 | N.D. | N.D. | N.D. | N.D. | N.D. | N.D. |
| | % | 0.33$^c$ | 0.92 | 1.50 | N.D. | N.D. | N.D. | N.D. | N.D. | N.D. |
| 120 IU | amt. released | 0.78 | 0.39 | 0.31 | 0.28 | 0.28 | 0.27 | 0.20 | N.D. | N.D. |
| | cumulative | 0.78 | 1.17 | 1.48 | 1.76 | 2.04 | 2.31 | 2.51 | N.D. | N.D. |
| | % | 0.65 | 0.98 | 1.23 | 1.47 | 1.70 | 1.93 | 2.09 | N.D. | N.D. |
| 900 IU | amt. released | 22.6 | 29.4 | 10.1 | 5.0 | 3.0 | 3.2 | 3.8 | N.D. | N.D. |
| | cumulative | 22.6 | 52.0 | 62.1 | 67.1 | 70.1 | 73.3 | 77.1 | N.D. | N.D. |
| | % | 2.51 | 5.78 | 6.90 | 7.46 | 7.79 | 8.14 | 8.57 | N.D. | N.D. |
| 1200 IU | amt. released | 89.0 | 51.0 | 21.6 | 9.2 | 18.2 | 14.4 | 6.9 | 7.5 | 4.7 |
| | cumulative | 89.0 | 140.0 | 161.6 | 170.8 | 189.0 | 203.4 | 210.3 | 217.8 | 222.5 |
| | % | 7.42 | 11.67 | 13.47 | 14.23 | 15.75 | 16.95 | 17.53 | 18.15 | 18.54 |

TABLE 2-continued

EPO release kinetics from collagen cuffs

| EPO amount loaded | | 1 | 3 | 5 | 7 | 10 | 14 | 21 | 28 | 35 |
|---|---|---|---|---|---|---|---|---|---|---|
| 1200 IU sustained release | amt. released | N.D. | N.D. | N.D. | N.D. | 3.7 | 3.9 | N.D. | N.D. | N.D. |
| | cumulative | N.D. | N.D. | N.D. | N.D. | 3.7 | 7.6 | N.D. | N.D. | N.D. |
| | % | N.D. | N.D. | N.D. | N.D. | 0.31 | 0.63 | N.D. | N.D. | N.D. |

[a] amount of EPO (IU) eluted into PBS
[b] cumulative amount of EPO (IU) released
[c] cumulative amount of EPO released as percentage of initial amount loaded
[d] N.D. = not determined The rate of release of EPO from the short- and intermediate-term release EPO/collagen matrices was biphasic. Not to be bound by theory, it is expected that a pool of EPO in the matrices was physically and mechanically entrapped with collagen fibers and diffused out of the matrix at a faster rate, as compared to another pool of EPO more strongly associated with the collagen molecules or fibers via ionic bonds.

For particular in vivo applications, the initial fast-releasing pool of EPO can be removed from the EPO/collagen matrices prior to implantation, e.g., by incubating them in saline at 37° C. for 3-7 days depending on the initial amount of EPO incorporated.

In a particular example, incubating a 1200 IU EPO/collagen cuff matrix in saline for 7 days yielded a cuff that released EPO at a relatively constant rate over a two-week period. See the data for the 1200 IU sustained release cuff listed in Table 2 above.

Example 8: Local Delivery of EPO and its Effects on Post-Surgery Latency Period

The efficacy of an EPO eluting EPO/collagen cuff matrix implant is tested in a rat sciatic nerve injury model. Briefly, a sciatic nerve in control and experimental animals is severed and treated by entubulation repair using a type I collagen nerve guide produced as described in Example 1 above. An EPO/collagen cuff matrix implant is applied to one end of the tubular nerve guide in experimental animals, and a collagen cuff matrix implant lacking EPO is applied to one end of the tubular nerve guide in the control group. Lewis rats are used, as this strain displays autophagia of the denervated limb less frequently than other rat species. See, e.g., Chamberlain, et al., 2000, J. Neurosci. Res. 60:666-677. A summary of the study is shown below in Table 3.

TABLE 3

Local EPO delivery animal study protocol summary

| Group | | Duration of implantation | No. of animals per group | Analysis (histology) |
|---|---|---|---|---|
| Experimental | 120 IU eluting cuff | 7 days 14 days | 6 6 | Proximal end of repair |
| Experimental | 480 IU eluting cuff | 7 days 14 days | 6 6 | Proximal end of repair |
| Experimental | 900 IU eluting cuff | 7 days 14 days | 6 6 | Proximal end of repair |
| Control | collagen cuff without EPO | 7 days 14 days | 6 6 | Proximal end of repair |

In detail, 48 adult Lewis rats (~200 g each) are anesthetized with an intraperitoneal injection of a mixture of ketamine HCl (90 mg/kg) and xylazine HCl (10 mg/kg), the hindquarters are shaved on the right side, scrubbed with betadine, and draped with a sterile towel while in the left side lying position. The right sciatic nerve of each animal is exposed through a longitudinal muscle splitting incision in the mid-thigh and dissected free from the underlying muscle bed. The sciatic nerve is transected with a sharp scissors at the mid-thigh level and a 2 mm segment resected. The proximal stump is inserted 2 mm into the lumen of one end of a 14 mm long type I collagen nerve guide (1.5 mm ID) and fixed in place with a single sling stitch of 9-0 resorbable PGA suture, e.g., VICRYL™. The distal nerve stump is inserted into the other end of the nerve guide and sutured in the same fashion, leaving a 10 mm gap between the nerve stumps.

Immediately upon transection of the sciatic nerve, nerve slack is lost due to retraction of the proximal and distal stumps. A nerve resection length of 2 mm is chosen such that the increase in nerve length upon suturing the nerve guide in the entubulation procedure balances the loss of nerve slack. As such, the procedure eliminates excessive tension on the newly repaired nerve. Further, resorbable PGA suture is used to minimize long-term inflammation.

In each experimental animal, one 5 mm length of fast-eluting EPO/Collagen cuff matrix (120 IU, 480 IU, or 900 IU/rat—12 rats per dose) is implanted on the outer surface of the nerve guide at the end where the proximal nerve stump is sutured. The inside diameter of the cuff is selected to loosely curl around the outside diameter of the nerve guide. A collagen cuff lacking EPO is implanted at the analogous site in 12 control rats. No suture is necessary to hold the cuff in place.

The muscle borders are approximated and sutured with 3-0 VICRYL™. The skin incision is closed with stainless steel staples. The dose range of EPO is selected based on the total EPO IU released for the first 7 days from the in vitro release studies.

Animals are euthanized at day 7 and day 14 after surgery by intraperitoneal injection of 150 mg/kg pentobarbital. Rats are trans-cardially perfused with phosphate buffered saline (pH 7.2) followed by 4% paraformaldehyde in 0.1 M phosphate buffer (pH 7.2). After perfusion, the implanted nerve guide is dissected out, post-fixed in 1% glutaraldehyde and 2% paraformaldehyde in 0.1 M phosphate buffer for 24 hours and treated for 1 h with 2% osmium tetroxide. Two micrometer transverse sections are cut at a defined distance from the cut end of the proximal nerve stump. The tissue slices are floated onto glass slides, stained with toluidine blue, and mounted before being cover-slipped.

Partially overlapping light microscopy images of the entire cross section of the nerve guide/sciatic nerve are captured using a digital camera and 40× objective and 100× oil immersion objective. The images are montaged using commercially available software and saved as one image of the entire section of the sciatic nerve. Every myelinated axon in the images are counted with Image J software. The length, number, diameter, and thickness of the myelin of myelinated axons are determined from the beginning of the cut end of the proximal stump to a predetermined distance from the cut end.

In addition, blood vessels, mast cells, macrophages, and other cell types were identified and quantified. One equivalent section of the contralateral sciatic nerve was processed in the same manner for a normal control.

Example 9: Longer-Term Effect of Local EPO Delivery on Nerve Repair

The longer term effect of EPO eluting EPO/collagen cuff matrix implants on the rate, number, and quality of myelinated axons across the entire length of a 10 mm nerve gap is assessed in the rat sciatic nerve injury model discussed above in Example 9. An EPO release time of 3-6 weeks is tested to give regenerated axons enough time to become myelinated and protected by EPO. One or two implants are used for each animal according to the protocol summary shown in Table 4 below.

TABLE 4

Longer-term animal study protocol summary

| Group | Time of implantation | No. of animals | Analysis (histology) |
| --- | --- | --- | --- |
| 1. Intermediate sustained EPO release implant (1,200 IU) | 3 weeks | 6 | Proximal and middle sections of repair |
| 1. | 6 weeks | 6 | Distal repair section |
| 2. Fast EPO release implant (900 IU) at the proximal end and intermediate sustained EPO release implant (1,200 IU) at the middle section and distal end | 3 weeks | 6 | Proximal and middle sections of repair |
| 2. | 6 weeks | 6 | Distal repair section |
| 3. Control implant (no EPO) | 3 weeks | 6 | Proximal and middle sections of repair |
| 3. | 6 weeks | 6 | Distal repair section |

To repeat from above, a 10 mm sciatic nerve gap is formed in rats after entubation repair with a collage nerve guide.

A first group of animals is treated by wrapping a single 14 mm length of an intermediate sustained release EPO eluting collagen cuff matrix around the middle of the nerve gap extending just beyond the distal nerve stump. As described in Example 7, this intermediate sustained release EPO/collagen cuff matrix is prepared by removing the fast releasing EPO from an implant by incubating it in saline for 3-7 days. The intermediate sustained release EPO/collagen cuff is dried until needed for implantation.

A second group of animals is treated with two implants at the same nerve injury site. A fast-eluting EPO/collagen cuff matrix (900 IU, 5 mm long) is rinsed with saline for two days and then wrapped around the proximal stump end of the entubation repair. A second 9 mm long intermediate sustained release EPO/collagen cuff matrix is also wrapped at the middle and distal portion as described in the preceding paragraph.

Collagen cuff matrices lacking EPO are wrapped around the entubated nerve in control animals.

The number of myelinated axons and the quality of myelination at two time points after implantation, i.e., 3 weeks and 6 weeks, are assessed by histology as described above in Example 8.

In particular, the number of myelinated axons and the thickness of myelination at the proximal and middle section of the repair are examined at the 3-week time point. At the 6 week time point, the number of myelinated axons and the thickness of myelination at the distal portion of the repair are measured. The measurements at the proximal stump are the same as that described in that described in Example 8.

Not to be bound by theory, the positive effect of EPO on the rate of axonal sprouting at the proximal stump is expected to improve the rate of nerve regeneration and subsequent myelination. Further, EPO should protect from degeneration both the proximal myelinated axons and also decrease distal axonal degeneration and scar tissue formation.

Example 10: The Effect of EPO on Functional Recovery

Functional recovery after nerve repair is assessed using a sciatic function index (SFI) as previously described in de Medinaceli et al., 1982, Exp. Neurol. 77:634-43 and later adapted and modified by Chamberlain et al.

Rats are subjected to nerve injury and entubation repair with or without EPO/collagen cuff matrices as described in Example 9. The two-cuff procedure (both proximal and middle/distal wraps) is used for this study. The SFI is calculated based on the results of walking track measurements as previously described. More specifically, at predetermined time points post-surgery, the rat's hind paws are dipped into black non-toxic water-soluble ink. The rats walk across a clean sheet of white paper that is placed in a walking chamber (10 cm wide×85 cm long) terminating in a dark box, leaving footprints from the hind limb. After several practice sessions, the rats walk straight to the end of the chamber to the dark box. Three footprint parameters are measured for analysis: (i) print length (PL), (ii) toe spread (TS), and (iii) intermediate toe spread (IT).

The initial measurements are modified according to Chamberlain et al. and used to calculate SFI according to the following equation:

$$SFI = -38.3(PLF) + 109.5(TSF) + 13.3(ITF) - 8.8$$

in which PLF, TSF and ITF represent the normalized foot print measurements (experimental value minus normal value divided by the normal value): print length factor (PLF), toe spread factor (TSF) and intermediate toe spread factor (ITF). The SFI is weighted so that normal function scores are approximately −10 and no function scores are approximately −110. See Chamberlain, et al.

Following walking track assessment of functional recovery, animals are euthanized and tissues processed as described in Example 8 above.

For tissue analysis, the nerve guide is dissected free, divided into proximal, middle, and distal segments of 3 mm in length, and processed for light microscopy as described above. One 3 mm section of the contralateral mid-thigh sciatic nerve is processed in the same manner for a normal control.

Partially overlapping images of the entire cross section of the nerve guide/sciatic nerve are captured and analyzed as set forth, supra.

Example 11: Repair of Critical Size Nerve Defects with EPO/Collagen Cuff

The effect of EPO on repair of a critical size defect is examined in the rat sciatic nerve model described above. As mentioned above, currently available peripheral nerve repair devices can only repair defects that do not exceed the critical length, i.e., 1 cm in rats and 2-2.5 cm in humans.

An EPO/collagen cuff matrix is employed in the rat sciatic nerve defect model described above in which the nerve gap is 1.5 cm, beyond the length of a critical defect.

The EPO/collagen cuff matrix described in Example 5 is used for this study. It is prepared initially with 900 IU of EPO incorporated into the collagen cuff matrix. Prior to implantation the cuff is rinsed for two days in saline to remove the fast-release pool of EPO, leaving only the sustained/slow release pool. EPO/collagen cuff matrices are subjected to ethylene oxide sterilization prior to implantation. The releasable dose level of EPO is 1-5 IU/rat/day over a period of 6-8 weeks.

The rat sciatic nerve injury model described above is employed using a total of 36 animals (250 g-300 g each) divided into three groups as shown in Table 5 below.

TABLE 5

Critical size defect experimental protocol

| Group | Time of implantation | No. of animals |
| --- | --- | --- |
| 1. Slow release EPO only | 8 weeks<br>16 weeks | 6<br>6 |
| 2. Fast release EPO cuff (7 mm) at proximal end and a slow release EPO cuff (12 mm) placed next to the fast release cuff | 8 weeks<br>16 weeks | 6 |
| 3. control cuff only- no EPO | 8 weeks<br>16 weeks | 6<br>6 |

A 1.5 cm nerve gap is created as set forth above. In Group 1, the slow release EPO/collagen cuff matrix (19 mm) is implanted across the entire length of the nerve guide. In Group 2, a fast release EPO/collagen cuff matrix (7 mm length) is positioned at the proximal stump region and the slow release EPO/collagen cuff matrix (12 mm length) is placed next to the fast release EPO/collagen cuff matrix, covering the middle section and the distal nerve stump. In control Group 3, collagen cuff matrices lacking EPO are positioned across the length of the nerve guide. All groups are evaluated at 8 weeks and 16 weeks post-surgery.

Functional testing and histological examination are performed as described above in Examples 8 and 10.

OTHER EMBODIMENTS

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An implantable drug-delivery device for repairing a severed peripheral nerve, the drug-delivery device comprising a matrix formed of a biopolymer and an erythropoietin (EPO) entrapped in the matrix, wherein, after in vivo implantation of the drug-delivery device, the EPO elutes over 1 day to 12 weeks and the EPO elutes in a biphasic manner.

2. The implantable drug-delivery device of claim 1, wherein the matrix is a porous de-cellularized biopolymer matrix of a mammalian peripheral nerve.

3. The implantable drug-delivery device of claim 1, wherein the matrix is semipermeable and the biopolymer is chitosan, alginic acid, cellulose, elastin, fibrin, a glycosaminoglycan, gelatin, a collagen, or a mixture thereof.

4. The implantable drug-delivery device of claim 3, wherein the biopolymer is collagen type I, type II, or type III.

5. The implantable drug-delivery device of claim 4, wherein the biopolymer is type I collagen.

6. The implantable drug-delivery device of claim 5, wherein the EPO elutes over 1 to 7 days.

7. The implantable drug-delivery device of claim 5, wherein the EPO elutes over 1 to 3 weeks.

8. The implantable drug-delivery device of claim 5, wherein the EPO elutes over 3 to 6 weeks.

9. The implantable drug-delivery device of claim 5, wherein the EPO elutes over 6 to 12 weeks.

10. The implantable drug-delivery device of claim 1, wherein the device is in the form of a tube, a tubular wrapping cuff, a sheet, a rod, a strip, or a sponge.

11. A method for repairing a severed peripheral nerve having a proximal stump and a distal stump, the method comprising:
providing an implantable drug-delivery device that includes a matrix formed of a biopolymer and an erythropoietin (EPO) entrapped in the matrix,
inserting the proximal stump and the distal stump into a nerve guide implant and stabilizing the nerve stumps with a suture, and
implanting the drug-delivery device at the site of the severed nerve, wherein, after implantation in vivo of the drug-delivery device, the EPO elutes over 1 day to 12 weeks and the EPO elutes in a biphasic manner.

12. The method of claim 11, wherein the matrix is a porous de-cellularized biopolymer matrix of a mammalian peripheral nerve and the implantable drug-delivery device is placed inside of the nerve guide implant prior to inserting the proximal stump and the distal stump.

13. The method of claim 11, wherein the matrix is semipermeable and the biopolymer is chitosan, alginic acid, cellulose, elastin, fibrin, a glycosaminoglycan, gelatin, a collagen, or a mixture thereof.

14. The method of claim 13, wherein the biopolymer is collagen type I, type II, or type III.

15. The method of claim 14, wherein the biopolymer is type I collagen.

16. The method of claim 15, wherein the EPO elutes over 1 to 7 days.

17. The method of claim 15, wherein the EPO elutes over 1 to 3 weeks.

18. The method of claim 15, wherein the EPO elutes over 3 to 6 weeks.

19. The method of claim 15, wherein the EPO elutes over 6 to 12 weeks.

20. The method of claim 11, wherein the device is in the form of a tube, a tubular wrapping cuff, a sheet, a rod, a strip, or a sponge.

21. The method of claim 20, wherein the drug-delivery device is affixed to an outer surface of the nerve guide implant.

22. The method of claim 20, wherein the drug-delivery device is affixed to an inner surface of the nerve guide implant prior to the attaching step.

23. The method of claim 11, wherein a gap between the proximal stump and the distal stump is 1 cm or less and the EPO elutes over 1 to 7 days.

24. The method of claim 11, wherein a gap between the proximal stump and the distal stump is 1 cm to 3 cm and the EPO elutes over 1 to 6 weeks.

25. The method of claim 11, wherein a gap between the proximal stump and the distal stump is 3 cm to 10 cm and the EPO elutes over 6 to 12 weeks.

* * * * *